United States Patent [19]

Walsh

[11] 4,251,541
[45] Feb. 17, 1981

[54] 1-SUBSTITUTED-3-ARYLTHIO-4-HYDROXYPYRROLIDINES

[75] Inventor: David A. Walsh, Richmond, Va.

[73] Assignee: A. H. Robins Company, Inc., Richmond, Va.

[21] Appl. No.: 2,103

[22] Filed: Jan. 9, 1979

[51] Int. Cl.³ .................... C07D 207/12; A61K 31/40
[52] U.S. Cl. ................................. 424/274; 260/326.46; 260/326.47; 260/326.5 S; 544/105
[58] Field of Search ...................... 260/326.47, 326.46, 260/326.5 S; 424/274

[56]  References Cited
U.S. PATENT DOCUMENTS 4,160,837  7/1979  Paioni .................................. 424/267

FOREIGN PATENT DOCUMENTS 2738477  3/1978  Fed. Rep. of Germany ...... 260/326.47

Primary Examiner—Mary C. Lee

[57]  ABSTRACT

Trans isomers of 1-substituted-3-arylthio-4-hydroxypyrrolidines and derivatives thereof having the formula:

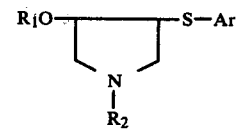

are disclosed wherein $R_1$ is hydrogen, lower-alkyl, —C(O)NH-lower-alkyl and —C(O)-NH-phenyl; $R_2$ is lower-alkyl, cycloalkyl and phenylalkyl; Ar is phenyl and substituted phenyl and the pharmaceutically acceptable addition salts thereof. The compounds have antidepressant activity in animals.

12 Claims, No Drawings

1-SUBSTITUTED-3-ARYLTHIO-4-HYDROXYPYRROLIDINES

BACKGROUND OF THE INVENTION

1. FIELD OF INVENTION

The present invention relates to certain novel trans isomers of 1-substituted-3-arylthio-4-hydroxypyrrolidine and derivatives thereof which are useful in treating depression in living animals with pharmaceutical compositions prepared therefrom.

2. DESCRIPTION OF THE PRIOR ART

Compounds of the present invention have not been available prior to the present invention. German Offenlegungsschrift No. 2,738,477 has disclosed certain trans-3-arylthio-4-hydroxypyrrolidines and piperidines which have pertinence to the present invention but which disclosure is subsequent to the present invention.

SUMMARY OF INVENTION

The present invention provides novel trans isomers of 1-substituted-3-arylthio-4-hydroxypyrrolidines and derivatives thereof which have important pharmacological activity as antidepressants in animals. The compounds of the invention are represented by the following structure formula:

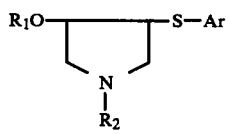

Formula I
(Trans isomers)

wherein;

$R_1$ is hydrogen, loweralkyl,

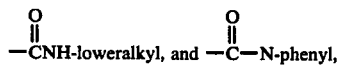

$R_2$ is loweralkyl, cycloalkyl and phenylalkyl,

Ar is phenyl and substituted phenyl, and the pharmaceutically acceptable addition salts thereof.

Antidepressant activity was shown to be present by the procedure given by Englehardt, E. L. et al, J. Med. Chem. 11 (2): 325 (1968) wherein the novel compounds of the present invention were administered to mice intraperitaneally and the effectiveness of the compounds in blocking the depressant effects which are induced in mice by intravenous administration of 2-oxo-3-isobutyl-9,10,-dimethoxy-1,2,3,4,6,7-hexahydro-11bh-benzo[a]quinolizine (tetrabenazine) was determined. The compound free base of Example 2; namely, trans-1-ethyl-4-phenylthio-3-pyrrolidinol is preferred for its antidepressant effect having exhibited an $ED_{50}$ of 5.0 mg/kg in the antitetrabenazine test described in the foregoing.

It is accordingly an object of the present invention to provide novel trans-3-arylthio-4-hydroxypyrrolide compounds which have a high degree of antidepressant activity and methods of producing and using the compounds.

Another object is to provide a novel method for the treatment of living animals and especially mammalian animals for the purpose of relieving anxiety and depression.

Additional objects will be apparent to one skilled in the art and still other objects will become apparent hereinafter.

DETAILED DESCRIPTION OF THE INVENTION

The present invention encompasses the novel trans isomers of 1-substituted-3-arythio-4-hydroxypyrrolidines and derivatives thereof as set forth hereinabove in Formula I and the definitions therewith as composition of matter and the utilization of these novel compounds in living animals for their pharmacological effect as set forth hereinabove and below.

The term "loweralkyl" as used in the specification and claims includes straight and branched chain radicals of up to eight carbon atoms inclusive and is exemplified by such groups as methyl, ethyl, propyl, isopropyl, butyl, isobutyl, tertiary butyl, amyl, isoamyl, hexyl, heptyl, octyl, and the like.

The term "substituted phenyl" as used in the specification and claims includes phenyl substituted in one to 3 positions by one or more radicals selected from halogen, O-loweralkyl, $NHC(O)CH_3$, $CF_3$, $—C(O)CH_3$, $—CH_2—CH=CH_2$, alkyl, hydroxy, $—OCH_2$-phenyl and $—C(O)NH_2$.

By "cycloalkyl" is meant cycloalkyl radicals having 1 to 9 carbon atoms and includes such radicals as cyclopropyl, cyclobutyl, cyclopentyl, cyclohexyl and the like.

Representative of phenylalkyl radicals are benzyl, α-methylbenzyl, phenylethyl, phenylpropyl, phenylbutyl, and the like.

The starting materials used in preparing the novel compounds of Formula I were 1-benzyl-3,4-epoxypyrrolidine and 1-ethyl-3,4-epoxypyrrolidine, which preparations are represented by the following equation:

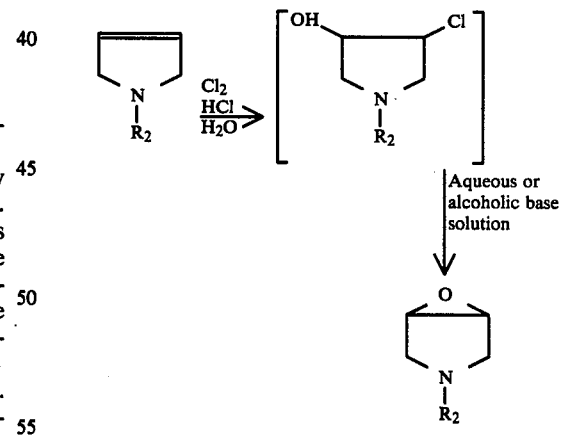

wherein $R_2$ is as defined hereinabove.

The pyrrolines used in these preparations are prepared according to the procedure of U.S. Pat. No. 3,691,198. Preparations 2–4 describe the actual synthesis of the 3,4-epoxypyrrolidines and Preparation 1 describes the preparation of 1-cyclohexyl-◁³-pyrroline.

PREPARATION 1

1-Cyclohexyl-◁³-pyrroline

A solution of 5.19 kg (52.3 moles) of cyclohexylamine in 4.0 liters of benzene was heated to mild reflux (92° C.) and then the heating discontinued. To the solution was added, dropwise, 1,635 g (13.1 moles) of 1,4-dichlorobutene at a rate sufficient to maintain gentle reflux, 3 hours time being required. Heating was continued and the reactants were heated at reflux temperature for 18 hours. The mixture was cooled to about 50° C. and filtered to remove the hydrochloride salt. Carbon dioxide was bubbled into the filtrate to precipitate excess amine carbonate salt which was removed by filtration. Solvent was removed from the filtrate by distillation under reduced pressure and the reddish fluid residue slightly contaminated with benzene weighed 1.506 g (76.2 yield).

PREPARATION 2

1-Cyclohexyl-3,4-epoxypyrrolidine Oxalate

A solution of 151.3 g (1.0 mole) of N-cyclohexyl-◁³-pyrroline, 100 ml of concentrated hydrochloric acid and 1.8 L of water was treated with a steam of chlorine gas until uptake ceased (6 hrs). The solution was washed with methylene chloride and the acidic solution was left standing overnight. The solution was then made basic with 50% sodium hydroxide and extracted with methylene chloride. The combined extracts were concentrated to give 185 g of chlorohydrin as residue. The residue was slowly poured into a 20% sodium hydroxide ethanol solution. The mixture was stirred for 0.5 hr and then 3.5 L of water was added. The mixture was extracted with methylene chloride and the combined extracts were dried over sodium sulfate and concentrated to give 154 g (92%) of amine epoxide. An NMR analysis indicates this residue is 86% epoxide and 14% 3,4-dichloro-N-cyclohexlpyrrolidine. The residue was vacuum distilled to give the epoxide as a water-white liquid, b.p. 70° at 0.6 mm. A portion of the liquid was converted to the oxalate to give white solid, m.p. 155°–6° C. when recrystallized from ethanol.

Analysis: Calculated for $C_{12}H_{19}NO_5$: C, 56.02; H, 7.44; N, 5.44. Found: C, 56.05; H, 7.50; N, 5.34.

PREPARATION 3

1-Benzyl-3,4-epoxypyrrolidine Oxalate

A mixture of 31.8 g. (0.20 mole) of N-benzyl-$\Delta^3$-pyrroline, 25 l. of concentrated hydrochloric acid and 300 ml. of water was treated with a stream of chlorine gas for 2 hr. The solution was filtered and the filtrate was made basic with 20% sodium hydroxide. The basic solution was extracted with three 150 ml portions of methylene chloride. The combined methylene chloride extracts were dried over magnesium sulfate and evaporated to give 48.5 g. of crude chlorohydrin as a dark oil. This oil was stirred with 200 ml. of 20% sodium hydroxide for 0.5 hr., 700 l. of water was added, and the base was extracted with four 100-ml portions of methylene chloride. The combined methylene chloride extracts were dried over magnesium sulfate and concentrated to yield 34.9 g (99%) of crude epoxide as a dark oil. The oxalate salt was prepared in 81% yield. Recrystallization from 95% ethanol gave the salt as offwhite needles, m.p. 148°–49°/d.

Analysis: Calculated for $C_{13}H_{15}NO_5$: C, 58.86; H, 5.70; N, 5.28. Found: C, 58.55; H, 5.68; N, 5.25.

PREPARATION 4

1-Ethyl-3,4-epoxypyrrolidine Oxalate

A mixture of 61 g. (0.63 mole) of 1-ethylpyrroline, 50 ml of concentrated aqueous HCl, and 600 ml of water was treated with chlorine gas for 2.5 hr. The mixture was filtered through cotton and the filtrate was washed with two 100-ml portions of methylene chloride. The aqueous layer was made basic with 20% sodium hydroxide, heated on a steam bath for 0.5 hr. and extracted with three 100-ml portions of methylene chloride. The combined extracts were dried over anhydrous sodium sulfate and concentrated and the residue vacuum distilled to give 39.4 g. (56%) of the epoxide as a clear oil (b.p. 75°–90° at 28 mm). The epoxide was converted to the oxalate and the salt was recrystallized from absolute ethanol to give white needles, m.p. 142°–4° d.

Analysis: Calculated for $C_3H_{13}NO_5$: C, 47.29; H, 6.45; N, 6.89. Found: C, 47.12; H, 6.42; N, 6.82.

Synthesis of the trans-isomers compounds of Formula I are primarily formed by reaction of 1-substituted-3,4-epoxypyrrolidines with arylsulfides as exemplified by the following equation:

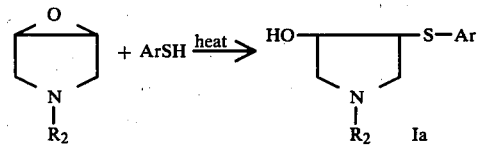

wherein $R_2$ and Ar are as defined hereinabove. Compounds of Formula Ia are further reacted with isocyanates to prepare compounds of Formula Ib according to the following equation:

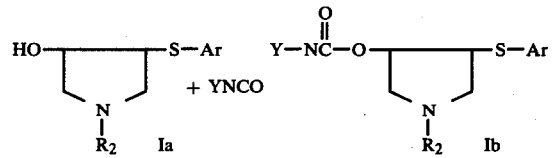

wherein Y=lower-alkyl or phenyl.

The novel compounds of the present invention and the novel process is exemplified more fully by the following illustrative examples. The scope of the invention is, however, not limited thereto.

EXAMPLE 1

Trans-1-Phenylmethyl-4-phenylthio-3-pyrrolidinol

A mixture of 8.8 g. (0.05 mole) of 1-benzyl-3,4-epoxypyrrolidine, 6.0 g. (0.055 mole) of thiophenol, and 3 drops of water was heated on a steam bath overnight. Upon cooling the mixture, a solid crystallized. The solid was dissolved in methylene chloride and the methylene chloride solution was washed with two 50-ml portions of 5% sodium hydroxide. The methylene chloride layer was dried over anhydrous sodium sulfate and concentrated to give a yellow oil which solidified on standing. The solid was recrystallized from cyclohexane to give 8.6 g. (60%) of a tan solid, m.p. 97°–99°.

Analysis: Calculated for $C_{17}H_{19}NOS$: C, 71.54; H, 6.71; N, 4.90. Found: C, 71.42; H, 6.75; N, 4.96.

EXAMPLE 2

Trans-1-Ethyl-4-phenylthio-3-pyrrolidinol Oxalate

An exothermic reaction occurred when 20.2 g. (0.18 mole) of N-ethyl-3,4-epoxypyrrolidine and 19.7 g. (0.18 mole) of thiophenol were mixed. A drop of conc. hydrochloric acid was added and the reaction became vigorous. The mixture was heated on a steam bath overnight. The gum was dissolved in methylene chloride and the solution was washed with two 100-ml portions of 5% sodium hydroxide and one 100-ml portion of water, dried over anhydrous sodium sulfate and concentrated to give 28 g. of oil as residue. This residue was subjected to vacuum distillation to remove the 3,4-dichloropyrrolidine impurity. The pot residue was converted to the oxalate in yield of 28.0 g. (50%) as a white solid, m.p. 114.5°–116.5°.

Analysis: Calculated for $C_{14}H_{19}NO_5S$: C, 53.66; H, 6.11; N, 4.47. Found: C, 53.55; H, 6.16; N, 4.42.

EXAMPLE 3

Trans-4-[(2-Chlorophenyl)thio]-1-ethyl-3-pyrrolidinol

A mixture of 11.3 g. (0.1 mole) of crude 1-ethyl-3,4-epoxypyrrolidine, 14.4 g. (0.1 mole) of 2-chlorothiophenol and 1 drop concentrated hydrochloric acid on a steam bath overnight. The reaction mixture was dissolved in methylene chloride and the solution was washed with two 100-ml portions of 5% sodium hydroxide and once with water. The methylene chloride layer was dried over anhydrous sodium sulfate and concentrated to give 23.8 g. of dark oil as residue which solidified when scratched with petroleum ether. The solid was collected by filtration and recrystallized from cyclohexane to yield 10 g. (39%) of tan solid, m.p. 90.5°–92.5°.

Analysis: Calculated for $C_{12}H_{16}ClNOS$: C, 55.91; H, 6.26; N, 5.43. Found: C, 56.13; H, 6.31; N, 5.40.

EXAMPLE 4

Trans-1-Ethyl-4-[(4-methylphenyl)thio]-3-pyrrolidinol

A mixture of 17.0 g. of 1-ethyl-3,4-epoxypyrrolidine and 19.0 g. of thiophenol was heated at 100° for 1 hr. The mixture crystallized on cooling and was recrystallized from cyclohexane-isooctane with charcoaling. The yield of product melting at 56°–8° was 59%.

Analysis: Calculated for $C_{13}H_{19}NOS$: C, 65.78; H, 8.07; N, 5.90. Found: C, 65.79; H, 8.04; N, 5.86.

EXAMPLE 5

Trans-1-Ethyl-4-[(4-methylphenyl)thio]-3-pyrrolidinolethylcarbamate (ester)

A mixture of 6.6 g. of 1-ethyl-4-(4-methylphenylthio)-3-pyrrolidinol and 6 g. of ethyl isocyanate in 60 ml. of benzene was stirred for 65 hr. Benzene and excess ethyl isocyanate were removed under vacuum and the product crystallized. It was recrystallized from petroleum ether. The yield of product melting at 58°–61° was 88%.

Analysis: Calculated for $C_{16}H_{24}N_2O_2S$: C, 62.31; H, 7.84; N, 9.08. Found: C, 62.32; H, 7.80; N, 9.08.

EXAMPLE 6

Trans-1-Ethyl-4-[(4-methylphenyl)thio]-3-pyrrolidinol Phenylcarbamate (ester) Hydrobromide A mixture of 6.5 g. of 1-ethyl-4-(4-methylphenylthio)-3-pyrrolidinol and 3.5 g. of phenylisocyanate in 60 ml. of benzene was stirred for 1 hr., then refluxed for 30 min. The benzene was removed and the residue was chromatographed on silica gel using EtOAc to elute the product. The hydro bromic acid salt was formed in ether and dried. The yield of product melting at 186°–9° was 87%.

Analysis: Calculated for $C_{20}H_{25}N_2O_2SBr$: C, 54.92; H, 5.76; N, 6.40. Found: C, 55.07; H, 5.76; N, 6.37.

EXAMPLE 7

Trans-1-Cyclohexyl-4-phenylthio-3-pyrrolidinol

Following the procedure of Example 1 but substituting 1-cyclohexyl-3,4-epoxypyrrolidine for 1-benzyl-3,4-epoxypyrrolidine, the title compound is obtained.

Formulation and Administration

Effective quantities of any of the foregoing pharmacological active compounds of Formula I may be administered to a living animal body for therapeutic purposes according to usual modes of administration and in usual forms, such as orally in solutions, emulsions, suspensions, pills, tablets and capsules in pharmaceutically acceptable carriers and parenterally in the form of sterile solutions.

For the parenteral administration the carrier or excipient may be a sterile, parenterally acceptable liquid; e.g., water or a parenterally acceptable oil; e.g., arachis oil contained in ampules.

Although very small quantities of the active materials of the present invention are effective when minor therapy is involved or in cases of administration to subjects having a relatively low body weight, unit dosages are usually from five milligrams or above and preferably 25, 50, or 100 milligrams or even higher, depending, of course, upon the emergency of the situation and the particular result desired. Twenty-five to 200 milligrams appears optimum per unit dose or usual broader ranges appear to be about 10 to 500 milligrams per unit dose. Daily dosages should preferably range from 1.0 to 20 mg/kg/day. The active ingredients of the invention may be combined with other pharmacologically active agents as stated above. It is only necessary that the active ingredient constitute an effective amount; i.e., such that a suitable effective dosage will be obtained consistent with the dosage form employed. Obviously, several unit dosage forms may be administered at about the same time. The exact individual dosages as well as daily dosages will, of course, be determined according to standard medical principles under the direction of a physician or veterinarian.

The following formulations are representative for all of the pharmacologically active compounds of this invention.

FORMULATIONS

1. Capsules

Capsules of 10 mg. and 50 mg. of active ingredient per capsule are prepared. With the higher amounts of active ingredient, reduction may be made in the amount of lactose.

| Typical blend for encapsulation | 10 mg. Per Capsule | 50 mg. Per Capsule |
| --- | --- | --- |
| Active ingredient, as salt | 10 | 50 |
| Lactose | 259 | 219 |
| Starch | 126 | 126 |
| Magnesium stearate | 4 | 4 |
| Total | 399 | 399 |

Additional capsule formulations preferably contain a higher dosage of active ingredient and are as follows:

| Ingredients | 100 mg. per Capsule | 250 mg. per Capsule | 500 mg. per Capsule |
|---|---|---|---|
| Active ingredient, as salt | 100 | 250 | 500 |
| Lactose | 214 | 163 | 95 |
| Starch | 87 | 81 | 47 |
| Magnesium stearate | 4 | 6 | 8 |
| Total | 399 | 500 | 650 |

In each case, uniformly blend the selected active ingredient with lactose, starch, and magnesium stearate and encapsulate the blend.

2. Tablets

A typical formulation for a tablet containing 5.0 mg. of active ingredient per tablet follows. The formulation may be used for other strengths of active ingredient by adjustment of weight of dicalcium phosphate.

| | Per Tablet, mg. |
|---|---|
| 1. Active ingredient | 10.0 |
| 2. Corn starch | 15.0 |
| 3. Corn starch (paste) | 12.0 |
| 4. Lactose | 35.0 |
| 5. Dicalcium phosphate | 132.0 |
| 6. Calcium stearate | 2.0 |
| Total | 202.0 |

Uniformly blend 1, 2, 4 and 5. Prepare 3 as a 10 percent paste in water. Grnaulate the blend with starch paste and pass the wet mass through an 8 mesh screen. The wet granulation is dried and sized through a 12 mesh screen. The dried granules are blended with the calcium stearate and compressed.

| 3. Injectable - sterile solution | | Per cc |
|---|---|---|
| Active ingredient | mg. | 20 |
| Preservative, e.g. chlorobutanol, w/vol. percent | | 0.5 |
| Water for injection q.s. | | |

Prepare solution, clarify by filtration, fill into vials, seal and autoclave.

Various modifications and equivalents will be apparent to one skilled in the art and may be made in the compounds, compositions and methods of the present invention without departing form the spirit and scope thereof, and it is therefore understood that the invention is to be limited only by the scope of the appended claims.

What is claimed is:

1. A compound selected from 1-substituted-3-arylthio-4-hydroxypyrrolidines and derivatives thereof having the formula:

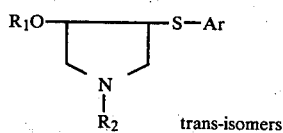

wherein;
R$_1$ is hydrogen, loweralkyl,

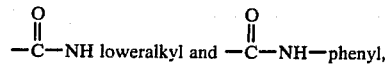

R$_2$ is loweralkyl, cycloalkyl and phenylalkyl,
Ar is phenyl and phenyl substituted by halogen, O-loweralkyl, —NHC(O)(CH$_3$), CF$_3$, —C(O)CH$_3$, —CH$_2$—CH=CH$_2$, alkyl, hydroxy, —OCH$_2$-phenyl and —C(O)NH$_2$, and the pharmaceutically acceptable acid addition salts thereof.

2. The compound of claim 1 which is trans-1-phenylmethyl-4-phenylthio-3-pyrrolidinol.

3. The compound of claim 1 which is trans-1-ethyl-4-phenylthio-3-pyrrolidinol.

4. The compound of claim 1 which is trans-1-ethyl-4-phenylthio-3-pyrrolidinol oxalate.

5. The compound of claim 1 which is trans-4-[(2-chloro phenyl)thio]-1-ethyl-3-pyrrolidinol.

6. The compound of claim 1 which is trans-1-ethyl-4-[(4-methylphenyl)thio]-3-pyrrolidinol.

7. The compound of claim 1 which is trans-1-ethyl-4[(4-methylphenyl)thio]-3-pyrrolidinoethylcarbamate (ester).

8. The compound of claim 1 which is trans-1-ethyl-4-[(4-methylphenyl)thio]-3-pyrrolidinolcarbamate (ester) hydrobromide.

9. A pharmaceutical composition for treating depression in animals in unit dosage form comprising (a) an effective amount of a 1-substituted-3-arylthio-4-hydroxypyrrolidine and derivatives thereof having the formula:

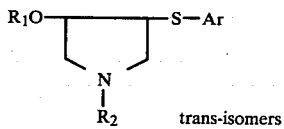

wherein
R$_1$ is hydrogen, loweralkyl,

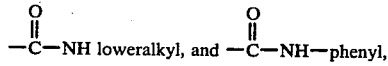

R$_2$ is loweralkyl, cycloalkyl and phenylalkyl,
Ar is phenyl and phenyl substituted by halogen, O-loweralkyl, —NHC(O)CH$_3$, CF$_3$, —C(O)CH$_3$, —CH$_2$—CH=CH$_2$, alkyl, hydroxy, —OCH$_2$-phenyl and —C(O)NH$_2$,
the pharmaceutically acceptable acid addition salts thereof, and (b) a pharmaceutical carrier therefor.

10. The composition of claim 9 wherein the compound is trans-1-ethyl-4-phenylthio-3-pyrrolidinol.

11. A method of treating depression in an animal which comprises administrating to an animal in need thereof an effective amount for treating depression of a compound having the formula:

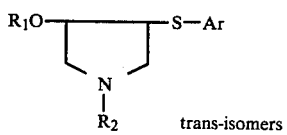

wherein
R$_1$ is hydrogen, loweralkyl,

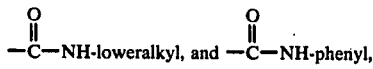
R₂ is loweralkyl, cycloalkyl and phenylalkyl,
Ar is phenyl and phenyl substituted by halogen, O-lower-alkyl, —NH—C(O)CH₃, CF₃, —C(O)CH₃, —CH₂—CH=CH₂, alkyl, hydroxy, —OCH₂-phenyl and —C(O)NH₂, and the pharmaceutically acceptable acid addition salts thereof.
12. The method of claim 11 wherein the compound is trans-1-ethyl-4-phenylthio-3-pyrrolidinol.
* * * * *